United States Patent [19]

Rheinberger et al.

[11] Patent Number: 5,886,064

[45] Date of Patent: *Mar. 23, 1999

[54] FINE-GRAINED POLYMERIZABLE COMPOSITIONS FLOWABLE UNDER PRESSURE OR SHEAR STRESS

[75] Inventors: Volker Rheinberger, Vaduz; Norbert Moszner, Eschen, both of Liechtenstein; Thomas Voelkel, Lindau, Germany; Peter Burtscher, Nuetziders, Austria

[73] Assignee: Ivoclar AG, Liechtenstein

[ * ] Notice: This patent issued on a continued prosecution application filed under 37 CFR 1.53(d), and is subject to the twenty year patent term provisions of 35 U.S.C. 154(a)(2).

[21] Appl. No.: 568,260

[22] Filed: Dec. 6, 1995

[30] Foreign Application Priority Data

Dec. 8, 1994 [DE] Germany .......................... 44 43 702.1

[51] Int. Cl.$^6$ .............................. C08F 293/00; C08F 2/44
[52] U.S. Cl. .......................... 523/116; 523/115; 523/117; 524/357; 524/358; 524/359; 524/538; 524/611; 524/612; 424/DIG. 16
[58] Field of Search ..................................... 523/115, 116, 523/117; 424/DIG. 16; 524/611, 612, 538, 357, 358, 359

[56] References Cited

U.S. PATENT DOCUMENTS

| 4,568,737 | 2/1986 | Tomalia et al. . |
| 5,318,999 | 6/1994 | Mitra et al. ............................ 523/115 |
| 5,354,785 | 10/1994 | Rheinberger et al. . |
| 5,418,301 | 5/1995 | Hult et al. ............................... 528/279 |
| 5,426,134 | 6/1995 | Rheinberger et al. . |

FOREIGN PATENT DOCUMENTS

| 0 449 399 A2 | 10/1991 | European Pat. Off. . |
| 0 480 472 A2 | 4/1992 | European Pat. Off. . |
| 0 576 112 A1 | 12/1993 | European Pat. Off. . |
| 4029230 A1 | 3/1992 | Germany . |
| WO 93/14147 | 7/1993 | WIPO . |

Primary Examiner—Andrew E. C. Merriam
Attorney, Agent, or Firm—Nixon, Hargrave, Devans & Doyle LLP

[57] ABSTRACT

A granular, polymerizable composition which contains at least one polymerizable monomer and/or oligomer and a polymerization initiator and optionally an accelerator and at least 70% by wt. filler and additionally 0.5 to 28% by wt. dendrimer and which becomes flowable under compressive or shear stress. The composition can be packed in similar manner to amalgam and is particularly suitable as dental material or for the production of a dental material.

15 Claims, No Drawings

FINE-GRAINED POLYMERIZABLE COMPOSITIONS FLOWABLE UNDER PRESSURE OR SHEAR STRESS

The present invention relates to highly-filled, granular, dendrimer-containing, polymerizable compositions which become flowable under compressive and/or shear stress and thus mouldable. The compositions according to the invention are suitable in particular as dental materials or for the production of dental materials.

Polymerizable compositions are used in many fields, inter alia both as dental materials and as adhesive and filler compositions. With a view to the stability of the cured composition as high a filler content as possible is generally aimed at. Polymerizable compositions with high filler contents, which are suitable as dental materials, are for example described in the International Encyclopedia of Composites (S. M. Lee, Publisher, Vol. 2, VCH-Verlagsgesellschaft, New York 1990, page 182) and by L. Ehrnford (Swed. Dent. J., Suppl. 18, 1983). On the other hand, highly-filled materials can be plastically moulded only with difficulty, which makes their subsequent processing difficult and limits the maximum filler content. Known from EP-OS 0 480 472 are curable polymer materials which are so highly filled that they can be processed only when exposed to ultrasonic vibrations.

WO93/17060 relates to dendritic macromolecules based on polyesters, which are characterized more by a highly-branched (hyper-branched) structure instead of an ideally branched dendrimer structure, and to processes for their production. The dendrimers are suitable inter alia as a component for polymerizable compositions, although only liquid varnishes are described in WO93/17060, while filler-containing compositions are not disclosed.

WO93/14147 relates to dendrimeric macromolecules whose branches are formed by vinyl cyanide units, and to processes for their production. These dendrimers are suitable inter alia for mixing with thermoplastic polymers or polymeric compositions. Dendrimers with polymerizable groups or highly-filled mixtures are not mentioned.

Polymerizable compositions which have such a high filler content that they have a granular structure instead of a highly viscous consistency and yet are adequately plastically mouldable are not known to date.

It is the object of the invention to provide a polymerizable composition with granular consistency which becomes flowable under compressive and/or shear stress and thus becomes mouldable and which is suitable in particular for use as dental material or for producing a dental material.

This object was surprisingly achieved by a polymerizable composition which, in addition to at least one polymerizable monomer and/or oligomer and at least one filler and a polymerization initiator and optionally an accelerator, contains 0.5 to 28% by wt. of a dendrimer. The filler content of the compositions according to the invention is at least 70% by wt. These compositions have a granular consistency, but become flowable and mouldable under compressive and/or shear stress.

Dendrimers are three-dimensional, highly-ordered oligomeric and polymeric compounds which are synthesized starting from small initiator molecules by a reaction sequence which is continually repeated. Suitable as initiators are monomeric or polymeric molecules with at least one functionality. These are reacted in a single or multi-stage reaction with a reactant which adds to the functionality of the initiator and which provides at least two new functionalities. The reaction of initiator and reactant produces the core cell (generation zero). By repeating the reaction, the functionalities of the first reactant layer are reacted with further reactants, at least two new branching centres being again introduced into the molecule in each case (1st generation). The progressive branching leads to a geometric growth in the number of atoms for each generation. Since the overall size can grow only linearly because of the number of possible covalent bonds determined by the reactants, the molecules become more packed from generation to generation and they change their shape from starfish-shaped to spherical. It is possible to allow such dendrimers to grow to a self-limiting size ("self-limiting generation"). The self-limiting size is determined by the number of functionalities of the initiator and of the repeat units and the dimensions of the individual components. Through the choice of these parameters it is possible to control the size, shape, topology, flexibility and surface chemistry of the dendrimers. A high initiator core multiplicity, a high multiplicity of the branching centres and short branching segment lengths produce very compact macromolecules with small cavities whilst on the other hand a low initiator core multiplicity, a low multiplicity of the branching centres and a long segment length lead to the formation of large cavities. At a given initiator core multiplicity, multiplicity of the branching centres and branching segment length, the internal surface increases with the number of generations.

Dendrimers preferred according to the invention are obtained by reacting hydroxyl- or amino group-containing initiator molecules with vinyl cyanides, such as acrylo- or methacrylonitrile (propylenimine dendrimers). Suitable propylenimine dendrimers and processes for their production are described in WO93/14147. Other groups of preferred dendrimers are the polyethers/polythioether dendrimers (A. B. Padias et al.; Polym. Prep. Am. Chem. Soc., Div. Polym. Chem. 30 (1989) 119), the polyester dendrimers (WO93/17060), the polyphenylenamide dendrimers (S. C. E. Backson et al.; Macromol. Symp. 77 (1994) 1) and the polyphenylene ester dendrimers (K. L. Wooley et al., Polymer Journal 26 (1994) 187). Mixtures of the cited dendrimers are also suitable.

Dendrimers which have a spherical structure are also preferred. In addition, dendrimers of the 4th or of a higher generation are particularly suitable according to the invention.

In a preferred embodiment the dendrimers have polymerizable terminal groups. The reactive groups of the last reactant generation are called terminal groups. Preferred polymerizable groups are (meth)acrylic, allyl, styryl, vinyl, vinyloxy and/or vinylamine groups.

The synthesis of dendrimers with polymerizable terminal groups takes place by the reactions, known from organic chemistry, of the aforementioned dendrimers with suitable monomer reagents. Particularly suitable starting materials are dendrimers with carboxyl, hydroxyl and/or amino terminal groups. Methacrylic acid chloride and isocyanatoethyl methacrylate are preferred for reacting hydroxy- or amino-functionalized dendrimers and 2-hydroxy ethyl methacrylate for reacting carboxyl group-containing dendrimers. The Michael reaction with acryloyloxy ethyl methacrylate (AEMA) is particularly preferred for reacting amino group-containing dendrimers. The Michael reaction takes place selectively at the acrylate double bond, whilst the methacrylate double bond is retained as polymerizable group.

The polymerizable compositions according to the invention are produced by mixing the dendrimer with at least one polymerizable monomer and/or oligomer. This mixture is then mixed in portions with a filler until it has a pasty consistency. In addition, a polymerization initiator, preferably a photoinitiator, and optionally an accelerator is added to the mixture.

Used as polymerizable monomer and/or oligomer are preferably mono- or polyfunctional methacrylates. Particularly preferred monomers are methyl methacrylate, triethylene glycol dimethacrylate, hexanediol methacrylate, dodecanediol dimethacrylate, bisphenol-A-dimethacrylate, bisphenol-A-glycidyl dimethacrylate, trimethylol propane trimethacrylate and 2-hydroxyethyl methacrylate and urethane dimethacrylates, i.e. products obtained by reacting isocyanates, in particular di- and/or triisocyanates, with hydroxyl group-containing methacrylates. Particularly preferred are bisphenol-A-diglycidyl dimethacrylate and the urethane dimethacrylate obtained from 2-hydroxyethyl methacrylate and 2,2,4-trimethyl hexamethylene diisocyanate-1,6. The monomer and/or oligomer content of the compositions according to the invention is preferably 0.5 to 28% by wt., particularly preferably 5 to 20% by wt.

Particularly suitable as fillers are amorphous silicas, in particular pyrogenic and precipitated silica having a BET surface area of 30 to 300 m²/g, preferably 30 to 100 m²/g (e.g. Aerosil 200, Ox 50; Degussa AG), or zinc oxide (ZnO).

A quite particularly preferred filler is an amorphous, spherical material based on silica which also contains at least one oxide of a metal of Groups I, II, III and IV of the periodic system. Strontium oxide and/or zirconium oxide is preferably used. The average primary particle size is in the range from 0.1 to 1.0 μm, in particular 0.15 to 0.5 μm. The refractive index of the material is between 1.50 and 1.58, in particular between 1.52 and 1.56. A particularly preferred value is 1.53±0.01. Filler mixtures can also be used provided that they satisfy the requirement as regards particle size and refractive index. Fillers of this type are disclosed in DE 32 47 800 C2 and are called spherosils within the scope of this invention. The filler can also be present sintered as a mixture of agglomerates with an average particle size of 1 to 30 μm.

Particularly suitable as X-ray-opaque fillers are X-ray-opaque glasses, barium sulphate and ytterbium fluoride. Mixtures of fillers, in particular of the cited X-ray-opaque and non-X-ray-opaque fillers, are also suitable. Particularly suitable filler mixtures are described in DE 40 29 230 A1, page 5, line 18 to page 6, line 27.

Inorganic fillers are preferably silanized in the usual manner with a silane, preferably with 3-methacryloyloxy propyl trimethoxy silane. The filler content of the polymerizable compositions according to the invention can be up to 92% by wt. It preferably lies in the range from 75% by wt. to 85% by wt.

Preferred initiators for the photopolymerization are benzophenone and benzoin and their derivatives. α-diketones are also suitable photoinitiators. 9,10-phenanthrenequinone, diacetyl- and 4,4'-dichlorobenzil are particularly preferred. Camphor quinone is quite particularly preferred.

α-diketones are preferably used in combination with accelerators, for example in combination with an amine as reducing agent. Preferred amines are cyanoethyl methylaniline (CEMA), dimethyl-aminoethyl methacrylate, triethanolamine and N,N-dimethyl-sym-xylidine. The ratio of photoinitiator to amine is generally 1:1. Most preferred is the use of 0.3% by wt. camphor quinone and 0.5% by wt. CEMA, relative to the total composition, as photoinitiator system.

Radical-supplying systems, for example benzoyl or lauryl peroxide together with amines, preferably N,N-dimethyl-sym-xylidine or N,N-dimethyl-p-toluidine, can be used as initiators for the cold polymerization.

Amino group-containing dendrimers can preferably act as amine accelerators.

A particularly preferred composition contains:

| % by wt. | Component |
|---|---|
| 18.3 | Monomer mixture comprising:<br>- Bisphenol-A-glycidyl methacrylate (39.2% by wt.); urethane dimethacrylate obtained from 2-hydroxyethyl methacrylate and 2,2,4-trimethyl hexamethylene diisocyanate-1,6 (20% by wt.);<br>- triethylene glycol dimethacrylate (20% by wt.);<br>- dendrimer (20% by wt.);<br>- camphor quinone (0.3% by wt.);<br>- CEMA (0.5% by wt.); |
| 67.2 | silanized, finely-dispersed silica; |
| 14.5 | ytterbium fluoride |

After mixing the components, air is removed from the material in the kneader by applying a vacuum. The pressure during air removal is preferably 5 to 20 mbar. The result is the formation of a granular, dry-looking material which, however, again becomes pasty and flowable under compressive or shear stress and can thus easily be fitted into moulds by hand, optionally with the aid of suitable instruments, such as a spatula, where it is then cured. The compositions according to the invention thus permit the complete and accurate filling of even small defects and gaps and are suitable in particular as dental materials, for example as tooth filling materials or for the production of dental materials for example for inlays/onlays, crowns, bridges and artificial teeth.

The decrease of the viscosity of the compositions according to the invention is probably attributable to the fact that under compressive or shear stress the dendrimers again release, like a molecular sponge, the monomer and/or oligomer absorbed into the dendrimer cavities during removal of air, so that the granular composition becomes a homogeneous mouldable material. A particular advantage of the compositions according to the invention is that they can be packed like an amalgam, as a result of which their handling is greatly simplified.

Curing the materials according to the invention preferably takes place by radical polymerization. This is preferably initiated thermally or photochemically. The crosslinking density and the properties of the cured material can be varied by the structure of the dendrimer used and/or by the type of monomer used. Thus, for example, by using less flexible monomers and/or dendrimers, the E-modulus of the cured materials can be increased. When flexible monomer and/or dendrimer components are used, materials with higher elongation, for example for provisional fillings are obtained. The invention is explained in more detail in the following with reference to examples.

EXAMPLES

Example 1

Modification of $DAB(PA)_{32}$ with AEMA 3.51 g (1 mmol) dendrimer $DAB(PA)_{32}$ (Company DSM, dendrimer based on polyethylenimine with 32 amino terminal groups, initiator: 1,4-diaminobutane (DAB)) in 5 ml methanol are mixed dropwise at approx. 8° C. with the exclusion of light with 10.61 g (58 mmol) AEMA (cf. J. Luchtenberg, H. Ritter, Macromol. Rapid. Commun. 15 (1994) 81) in 5 ml methanol. The mixture is stirred for one hour at room temperature and 24 hours at 60° C. and the methanol is then evaporated in vacuum. 14.6 g (95% yield; this and the following yields relate to the amount of dendrimer weighed in) of a clear liquid are obtained.

$^1$H-NMR (ppm, CDCl$_3$, 90 MHz): 1.6 (m, CH$_2$CH$_2$CH$_2$), 1.9 (s, CH$_3$ methacrylic), 2.3–2.5 (CH$_2$—N), 2.7 (broad t, CH$_2$CH$_2$CO$_2$), 3.6 and 4.3 (O—CH$_2$CH$_2$—O), 5.6 and 6.1 (2s,=CH$_2$).

stirred for one hour at room temperature and 24 hours at 60° C. and the methanol is then evaporated in vacuum. 33.5 g (99%) of a clear liquid are obtained.

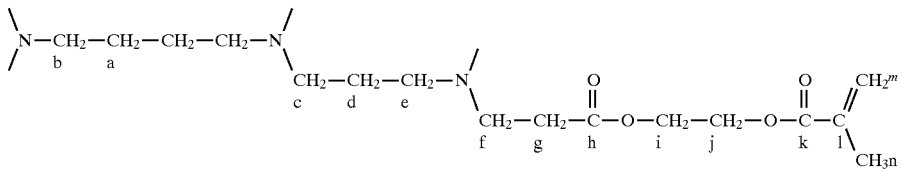

$^{13}$C-NMR (ppm, CDCl$_3$; 75 MHz): 24.24 (a); 51.82 (b); 51.41 (c); 32.25 (d); 49.04 (e); 61.00 (f); 66.26 (g); 167.61 (h); 61.95 (i); 62.32 (j); 172.82 (k); 135.91 (l); 125.91 (m); 18.19 (n).

IR (film, cm$^{-1}$): 2952 (C—H), 1724 (C=O).

Using concentration series in chloroform, the Mark-Houwink coefficient of the modified dendrimer is determined using a Ubelohde viscometer. The experimental value of α=0.211 comes very close to the theoretical value 0 for a spherical shape of the macromolecules in solution.

Example 2
Modification of DAB(PA)$_{16}$ with AEPA 15.46 g (0.02 mmol) DAB(PA)$_{16}$ (DSM, dendrimer based on polyethylenimine with 16 amino terminal groups) are reacted analogously to Example 1 with 58.94 (0.32 mol) AEMA. 77 g (99%) of a clear liquid are obtained.

Example 3
Modification of DAB(PA)$_{64}$ with AEMA 21.51 g (3 mmol) DAB(PA)$_{64}$ (DSM, dendrimer based on polyethylenimine with 64 amino terminal groups) are reacted analogously to Example 1 with 63.66 g (384 mmol) AEMA. 83.4 g (90%) of a clear liquid are obtained.

Example 4
Modification of DAB(PA)$_{32}$ with allyl acrylate 10.54 g (3 mmol) DAB(PA)$_{32}$ (DSM, dendrimer based on polyethylenimine with 32 amino terminal groups) are reacted analogously to Example 1 with 21.53 g (192 mmol) allyl acrylate in 5 ml methylene chloride. After evaporating off the solvent, 28.7 g (90%) of an oily liquid are obtained.

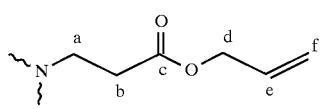

$^1$H-NMR (ppm, CDCl$_3$, 90 MHz): 4.57 d (OCH$_2$CH=), 5.8 m (CH=), 5.3 m (=CH$_2$).

$^{13}$C-NMR (ppm, CDCl$_3$, 75 MHz): 49.2 (a), 51.5 (b), 172.1 and 172.8 (c), 65.0 (d), 118.1 (e), 132.4 (f).

IR (film, cm$^{-1}$): 2948 (C—H), 1740 (C=O).

Example 5
Modification of DAB(PA)$_{32}$ with and ethyl acrylate 10.54 g (3 mmol) DAB(PA)$_{32}$ (Company DSH) in 10 ml methanol are mixed dropwise at approx. 8° C. with the exclusion of light with a mixture of 8.84 g (48 mmol) AEMA and 14.24 g (144 mmol) ethyl acrylate in 5 ml methanol (molar ratio AEMA:ethyl acrylate 1:3). The mixture is

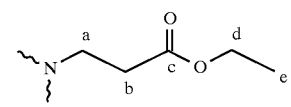

$^1$H-NMR (ppm, CDCl$_3$, 90 MHz): 1.3 (t, CH$_3$ ethyl); 1.7 (m, CH$_2$CH$_2$CH$_2$); 2.0 (s, CH$_3$ methacrylic) 2.4–2.5 (CH$_2$—N); 2.8(broad t, CH$_2$CH$_2$CO$_2$); 3.7 and 4.4 (O—CH$_2$CH$_2$—O), 4.2 (q, O—CH$_2$CH$_3$); 5.7 and 6.3; (=CH$_2$).

IR (film, cm$^{-1}$): 2952 (C—H), 1722 (C=O), 1636 (C=C), 1298, 1162 (C—O).

$^{13}$C-NMR (ppm, in CDCl$_3$, 75 MHz) 49.2 (a), 51.5 (b), 172.1 and 172.8 (c), 65.0 (d), 118.1 (e), 132.4 (f), 51.8 (g).

Example 6
Modification of DAB(PA)$_{64}$ with AEMA and trimethyl silyl ethylacrylate 10.75 g (1.5 mmol) DAB(PA)$_{64}$ (DSM, dendrimer of the 5th generation based on polyethylenimine with 64 amino terminal groups) in 5 ml methanol are mixed dropwise with a solution of 7.07 g (38.4 mmol) AEMA and 26.47 g (153.6 mmol) 2-trimethyl silyl ethyl acrylate in 5 ml methanol at 8° C. with the exclusion of light. The mixture is stirred for 1 hour at 8° C. and 24 hours at 60° C. and then volatile components were evaporated in the vacuum generated by a water-jet pump until no further weight change occured. 38.2 g (86%) of a viscous liquid are obtained.

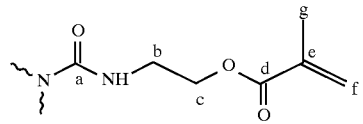

IR (KBr, cm$^{-1}$): 3353 (N—H), 2949 (C—H), 1731 (C=O).

$^1$H-NMR (ppm, CDCl$_3$, 90 MHz): 5.7 and 6.2 (2s, CH$_2$=), 4.1 (qu, OCH$_2$CH$_3$), 2.0 (s, CH$_3$ methacrylic), 1.2 (t, CH$_2$CH$_3$).

$^{13}$C-NMR (ppm, CDCl$_3$, 75 MHz): 172.4 (C=O, ethyl acrylate), 167.3 (C=O, methacrylate), 158.3 (C=O, urea), 136.3 and 125.6 (C=CH$_2$).

Example 7
Modification of DAB(PA)$_8$ with 2-isocyanatoethyl methyl acrylate (IEM)

5.41 g (7 mmol) DAB(PA)$_8$ (DSM, dendrimer based on polyethylenimine with 8 amino terminal groups) in 10 ml methylene chloride are mixed dropwise at 8° C. with the exclusion of light with 8.41 g (84 mmol) ethyl acrylate in 10 ml methylene chloride. The solution is stirred for one hour at 8° to 10° C. and 24 hours at 50° C. The mixture is then mixed dropwise with 4.34 g (28 mmol) IEM (Polyscience) at 18° to 22° C. The mixture is stirred for 5 days at room temperature and the solvent is then evaporated in vacuum. 17 g (94%) of a clear, viscous liquid are obtained.

Example 8
Reaction of $DAB(PA)_8$ with stearyl acrylate 5.9 g (7.6 mmol) $DAB(PA)_8$ (DSM) in 10 ml methylene chloride are added dropwise at 40° C. to 19.8 g (60 mmol) stearyl acrylate, which is obtainable according to the usual synthesis processes from stearyl alcohol and acrylic acid chloride, in 10 ml methylene chloride. The mixture is stirred for 24 hours at 46° to 48° C. and the solvent is then evaporated in vacuum. The vessel is aerated with dry air. 24.5 g (95%) of a wax-like solid (Mp.: 51°–52° C.) are obtained.

IR (KBr, $cm^{-1}$): 2916, 2850 (C—H), 1735 (C=O).
$^1$H-NMR (ppm, $CDCl_3$, 90 MHz): 1.3–1.5 (m, $CH_2$ of the stearyl chain), 1.0 (t, $CH_3$).
$^{13}$C-NMR (ppm, $CDCl_3$, 75 MHz): 172.7 (C=O)

Example 9
Reaction of $DAB(PA)_{32}$ with 2,2,3,4,4,4-hexafluorobutyl acrylate and AENA 5.27 g (1.5 mmol) $DAB(PA)_{32}$ (DSM) in 10 ml methanol are mixed dropwise at 8° to 10° C. with a mixture of 8.84 g (48 mmol) AEMA and 11.33 g (48 mmol) 2,2,3,4,4,4-hexafluorobutyl acrylate (Fluorochem) in 10 ml methanol. The solution is stirred for one hour at 8° to 10° C. and for 24 hours at 40° C. The volatile components are then evaporated at 30° C. in the vacuum of a water-jet pump until the weight was constant. 20.6 g (81%)of a clear, viscous liquid are obtained.

$$D-\overset{e}{\phantom{C}}-\overset{\phantom{O}}{\underset{d}{C}}-\overset{O}{\underset{\phantom{O}}{\overset{\|}{C}}}-\overset{b}{O}-CH_2-CF_2-\overset{a}{CHF}-CF_3$$

IR (KBr, $cm^{-1}$): 2953, 2816 (C—H), 1736 (C=O).
$^1$H-NMR (ppm, $CDCl_3$, 90 MHz): 4.6 (s, CHF), 3.8 (s, O—$CH_2$—$CF_2$).
$^{13}$H-NMR (ppm, $CDCl_3$, 75 MHz): 172.7 (C=O)

Example 10
Homopolymerization of the modified dendrimer from Example 1

The dendrimer according to Example 1 is mixed with stirring with one percent by weight of 2,2-azo-bis-(2-methyl-propionitrile) (AIBN) and the mixture is stirred until a homogeneous solution is obtained. Polymerization is monitored by means of differential scanning calorimetry (DSC) from 20° to 170° C. (heating rate: 10° C./min).
Results: Polymerization enthalpy: 49.8 kJ/mol Tg (glass transition temperature, polymer): −38.6° C. Polymerization shrinkage: 7.3% (from density measurements)

Example 11
Homopolymerization of the modified dendrimer from Example 3

The modified dendrimer from Example 3 is mixed with stirring with 1% by wt. of AIBN and the mixture is stirred until a homogeneous solution is obtained. Polymerization is monitored by means of DSC.
Results: Polymerization enthalpy: 55.1 kJ/mol Tg (polymer): 40.9° C. Polymerization shrinkage: 7.8% (from density measurements)

Example 12
Production of fine-grained materials 39.2% by wt. bis-phenol-A-glycidyl methacrylate, 20% by wt. urethane dimethacrylate (obtained from 2,2,4-trimethyl hexamethylene diisocyanate and hydroxyethyl methacrylate), 20% by wt. triethylene glycol dimethacrylate, 20% by wt. modified dendrimer according to Example 2, 0.30% by wt. camphor quinone and 0.50% by wt. cyanoethyl methylaniline (CEMA) are mixed in a kneading machine (Linden). 20 g of this monomer mixture are mixed in portions with silanized spherosil (PALFIQUE-S FILLER from Tokuyama Soda, Japan) as filler until the mixture has a pasty consistency (about 4 times the amount by weight of the monomer mixture). When a vacuum (15 mbar) is then applied, the paste dries within a few seconds and a fine-grained mixture results.

Example 13

In analogous manner to Example 12, a fine-grained material is produced using 20% modified dendrimer according to Example 1 and a mixture of silanized finely-dispersed silica and ytterbium fluoride in the ratio of 67.3 to 13.6 as filler. The material has the following composition: 18.33% by wt. monomer mixture (consisting of 39.2% by wt. bisphenol-A-glycidyl methacrylate, 20% by wt. urethane dimethacrylate (obtained from 2,2,4-trimethyl hexamethylene diisocyanate and hydroxyethyl methacrylate), 20% by wt. triethylene glycol dimethacrylate, 20% by wt. modified dendrimer, 0.30% camphor quinone and 0.50% by wt. CEMA), 67.12% by wt. silanized finely-dispersed silica (Aerosil OX 50, Degussa AG), 14.55% by wt. ytterbium fluoride. The dendrimer content of the total material is 7.2% by wt.

Example 14

A fine-grained material is produced analogously to Example 13 using 20% by wt. of the dendrimer according to Example 3. The composition of the material corresponds to that from Example 13.

Example 15

A fine-grained material is produced analogously to Example 14 but without CEMA, 0.5% by wt. more bisphenol-A-glycidyl methacrylate compared with Example 14 being added to compensate.

Example 16
(comparative example)

A flowable material is produced without dendrimer and without CEMA analogously to Example 14 and which has the following composition: 40.7% by wt. bisphenol-A-glycidyl methacrylate, 39% by wt. urethane dimethacrylate obtained from 2-hydroxyethyl methacrylate and 2,2,4-trimethyl hexamethylene diisocyanate-1,6, 20% by wt. triethylene glycol dimethacrylate and 0.3% by wt. camphor quinone.

Example 17
Light curing of granular dendrimer composite materials

The fine-grained composite from Example 12 is pressed by hand into testpiece moulds (2.5 mm×2.0 mm×2.0 mm) and the testpieces are then cured.

After curing, the testpieces are removed from the moulds and subjected to 24 hours' storage in water at 37° C. (according to ISO Standard 4049 (1988): Dentistry resin-based filling materials).

The cured testpieces are then investigated as to their mechanical properties. The results and the conditions chosen for the curing are summarized in Tables 1 and 2.

TABLE 1

Mechanical properties[1] of dental composite materials according to Examples 13 and 14

| | Composite material according to Example 14 | Composite material according to Example 13 |
|---|---|---|
| Bending strength (N/mm$^2$) after treatment A | 59 ± 7 | 51 ± 7 |
| Bending E modulus (N/mm$^2$) after treatment A | 5700 ± 500 | 5200 ± 600 |
| Bending strength (N/mm$^2$) after treatment B | 101 ± 12 | 96 ± 19 |
| Bending E modulus (N/mm$^2$) after treatment B | 12000 ± 2000 | 9400 ± 1100 |
| Compressive strength (N/mm$^2$) after treatment C | 176 ± 28 | 205 ± 35 |

[1]Determined according to ISO Standard 4049 (1988)

Treatment A: 2×60 sec. irradiation with a Heliolux®-GTE lamp (Vivadent)
Treatment B: 2×2 sec. irradiation with a Heliolux®-GTE lamp, 5 min post-curing by irradiation with a Spectramat® (Ivoclar AG) with simultaneous heating to 70° C.
Treatment C: 3×60 sec. irradiation with a Heliolux®-GTE lamp.

TABLE II

Light sensitivity and through-curing depth of dental composite materials with methacrylate-terminated dendrimer compared with a conventional composite

| | Composite material according to Comparative ex. 16 | Composite material according to Ex. 15 |
|---|---|---|
| Through-curing depth[1] | 4.6 mm | >6 mm |
| Light sensitivity[1] | 125 sec | 57 sec |
| Bending strength/Bending E modulus[1,3] | 66 ± 6 N/mm$^2$ 2400 ± 200 N/mm$^2$ | 43 ± 6 N/mm$^2$ 2400 ± 380 N/mm$^2$ |
| Through-curing depth[2] | 3.4 mm | 5.4 mm |
| Light sensitivity[2] | 125 sec | 70 sec |
| Bending strength/Bending E modulus[2,3] | 19 ± 2 N/mm$^2$ <500 N/mm$^2$ | 32 ± 11 N/mm$^2$ 250 N/mm$^2$ |

[1]without additional dye
[2]dyed according to tooth colour 310 of the Chromascop ® key, effective dye content: 0.03% by wt.
[3]determined according to ISO standard 4049 (1988)

We claim:

1. A granular, polymerizable composition comprising at least one polymerizable monomer and/or oligomer, a polymerization initiator, at least one filler, and a dendrimer, wherein said composition contains at least 70% by wt. of said filler, and 0.5 to 28% by wt. of said dendrimer and becomes flowable under pressure and/or shear stress and wherein said dendrimer is selected from the group consisting of a propylenimine, a polyether, a polythioether, a polyphenylenamide, and a polyphenylene ester dendrimer.

2. A granular, polymerizable composition according to claim 1, wherein the dendrimer has polymerizable terminal groups.

3. A granular, polymerizable composition according to claim 2, wherein the dendrimer comprises terminal groups selected from the group consisting of meth(acrylic), allyl, styryl, vinyl, vinyloxy, and vinylamine terminal groups.

4. A granular, polymerizable composition according to claim 1, which contains as the polymerizable monomer and/or oligomer one or more mono- or polyfunctional methacrylates.

5. A granular, polymerizable composition according to claim 1, which contains 0.5 to 28% by wt. of at least one polymerizable monomer and/or oligomer.

6. A granular, polymerizable composition according to claim 1, wherein the filler is selected from the group consisting of amorphous, pyrogenic and/or precipitated silica with a BET surface area of 30 to 300 m$^2$/g, zinc oxide (ZnO), X-ray opaque glass, barium sulphate, ytterbium fluoride and/or amorphous, spherical particles of silica with up to 20 mol % of an oxide of at least one element from Groups I, II, III and IV of the Periodic Table with a refractive index of 1.50 to 1.58 and with an average primary particle size of 0.1 to 1.0 μm.

7. A granular, polymerizable composition according to claim 1, which contains up to 92% by wt. filler.

8. A granular, polymerizable composition according to claim 1, wherein the initiator for photopolymerization is a photoinitiator selected from the group consisting of benzophenone, a benzophenone derivative, benzoin, and a benzoin derivative.

9. A granular, polymerizable composition according to claim 8, wherein the initiator for photopolymerization is an α-diketone.

10. A granular, polymerizable composition according to claim 1, wherein the initiator is a cold polymerization initiator comprising benzoyl or lauryl peroxide and additionally an amine.

11. A granular, polymerizable composition according to claim 1, wherein said composition further comprises an accelerator.

12. A dental material comprising a granular polymerizable composition according to claim 1.

13. A dental material according to claim 12, wherein the dental material is selected from the group consisting of artificial teeth, inlays, onlays, crowns, bridges, and tooth filling materials.

14. A granular, polymerizable composition comprising at least one polymerizable monomer and/or oligomer, a polymerization initiator, at least one filler, and a dendrimer, wherein said composition contains at least 70% by wt. of said filler, and 0.5 to 28% by wt. of said dendrimer and becomes flowable under pressure and/or shear stress, wherein said dendrimer has an ideally-branched dendrimer structure.

15. A granular, polymerizable composition according to claim 9 further comprising an amine.

* * * * *